United States Patent
Koulikov (10) Patent No.: US 10,234,381 B2
(45) Date of Patent: Mar. 19, 2019

(54) METHOD OF MEASURING THE RATIO OF ISOTOPOLOGUE CONCENTRATIONS IN THE GAS PHASE

(71) Applicant: Serguei Koulikov, Los Altos, CA (US)

(72) Inventor: Serguei Koulikov, Los Altos, CA (US)

(*) Notice: Subject to any disclaimer, the term of this patent is extended or adjusted under 35 U.S.C. 154(b) by 0 days.

(21) Appl. No.: 15/857,607

(22) Filed: Dec. 28, 2017

(65) Prior Publication Data
US 2019/0025201 A1   Jan. 24, 2019

Related U.S. Application Data

(60) Provisional application No. 62/535,505, filed on Jul. 21, 2017.

(51) Int. Cl.
| | | |
|---|---|---|
| G01N 21/00 | (2006.01) | |
| G01N 21/3504 | (2014.01) | |
| G01N 21/39 | (2006.01) | |
| G01N 21/17 | (2006.01) | |

(52) U.S. Cl.
CPC ......... *G01N 21/3504* (2013.01); *G01N 21/39* (2013.01); *G01N 2021/1748* (2013.01); *G01N 2021/399* (2013.01); *G01N 2201/0612* (2013.01)

(58) Field of Classification Search
CPC .. G01J 3/42; G01J 3/10; G01J 3/4338; G01N 21/00; G01N 21/3504; G01N 21/39; G01N 21/1702; G01N 33/0004
USPC ............... 356/432–440; 250/339.13
See application file for complete search history.

(56) References Cited

U.S. PATENT DOCUMENTS

| | | | |
|---|---|---|---|
| 4,684,805 A | | 8/1987 | Shu-ti Lee et al. |
| RE33,493 E | * | 12/1990 | Lee et al. ............ 250/343 |
| 5,146,294 A | | 9/1992 | Grisar et al. |
| 5,528,040 A | | 6/1996 | Lehmann |
| 5,543,621 A | | 8/1996 | Sauke et al. |
| 5,747,809 A | | 5/1998 | Eckstrom |
| 5,912,740 A | | 6/1999 | Zare et al. |
| 5,929,442 A | | 7/1999 | Higashi |
| 6,778,269 B2 | | 8/2004 | Fink et al. |
| 6,795,190 B1 | | 9/2004 | Paul et al. |
| 6,800,855 B1 | | 10/2004 | Dong et al. |

(Continued)

OTHER PUBLICATIONS

Gordon et al, The HITRAN2016 molecular spectroscopic database, Journal of Quantitative Spectroscopy & Radiative Transfer 203 (2017) 3-69, Elsevier Ltd.

*Primary Examiner* — Hoa Q Pham (57) ABSTRACT

Method of measuring a ratio of concentrations of two isotopologues of a chemical species in a first gas mixture using an optical absorption spectroscopy based gas analyzer; the method includes measuring the line intensity of a rotational-vibrational line of one isotopologue and the line intensity of another rotational-vibrational line of another isotopologue. The method also includes determining the ratio of two line intensities and comparing it with another ratio measured using another gas analyzer for a gas mixture with known concentration of isotopologues. The second ratio can be measured for the same pair of lines or for different pair of lines. The second ratio can be measured at the same gas temperature or at different gas temperature. The method includes determining a ratio of concentrations of two isotopologues based on two ratios of line intensities and two temperatures.

14 Claims, 4 Drawing Sheets

(56) References Cited

U.S. PATENT DOCUMENTS

| | | |
|---|---|---|
| 7,063,667 B1 | 6/2006 | Ben-Oren et al. |
| 7,245,380 B2 | 7/2007 | Kosterev |
| 7,450,240 B2 | 11/2008 | Morville et al. |
| 7,902,534 B2 | 3/2011 | Cole et al. |
| 8,327,686 B2 | 12/2012 | Kachanov et al. |
| 8,665,442 B2 | 3/2014 | Koulikov et al. |
| 8,681,336 B2 * | 3/2014 | Nickerson ............... G01N 21/85 356/402 |
| 8,823,923 B2 | 9/2014 | Berman et al. |
| 8,982,352 B1 | 3/2015 | Hoffnagle et al. |
| 9,097,583 B2 | 8/2015 | Gupta et al. |
| 9,200,960 B2 | 12/2015 | Mckeever et al. |
| 9,518,972 B2 | 12/2016 | Joseph et al. |
| 9,651,488 B2 | 5/2017 | Scherer et al. |
| 9,678,003 B2 | 6/2017 | Koulikov et al. |
| 9,759,654 B2 | 9/2017 | Koulikov et al. |
| 9,766,219 B2 * | 9/2017 | Wapelhorst ......... G01N 33/0011 |
| 9,829,432 B2 | 11/2017 | Maekawa et al. |
| 9,874,513 B2 * | 1/2018 | Schlueter ............ H01J 49/0009 |
| 9,983,056 B2 * | 5/2018 | Froehlich ............ H01S 5/06808 |
| 2003/0178589 A1 * | 9/2003 | Mori ..................... A61B 5/0836 250/573 |
| 2007/0077167 A1 * | 4/2007 | Mori .................. G01N 21/3504 422/54 |
| 2012/0298868 A1 | 11/2012 | Massick et al. |
| 2018/0136113 A1 * | 5/2018 | Bond .................. G01N 21/031 |

\* cited by examiner

METHOD OF MEASURING THE RATIO OF ISOTOPOLOGUE CONCENTRATIONS IN THE GAS PHASE

CROSS-REFERENCES TO RELATED APPLICATIONS

This application claims the benefit of, and priority to, U.S. provisional Patent Application No. 62/535,505 filed on Jul. 21, 2017 the contents of which are hereby incorporated by reference.

BACKGROUND OF THE INVENTION

The present invention relates generally to application of laser absorption spectrometry for isotope ratio analysis of gases and more specifically to laser absorption spectroscopy based systems and methods.

Optical absorption spectroscopy involves passing radiation through a sample, e.g., an analyte and measuring absorption property of the sample as a function of the radiation wavelength. For example, trace gas detection can be spectroscopically performed by taking measurements to detect the presence or absence of spectral absorption lines corresponding to the gas species of interest. Trace gas detection can be spectroscopically performed by taking measurements to quantify spectral absorption lines corresponding to the gas species of interest and to compute concentrations of analytes, gas pressure, and gas temperature. Spectroscopic analysis of isotopologues can also be performed. However, because the line intensities of rotational-vibrational lines are sensitive to the gas temperature, and the line shapes of those lines are also sensitive to the gas pressure and to gas composition, measurements of the isotopic ratio with high accuracy require highly accurate measurements of the analyzed gas temperature and pressure. Moreover, because the natural abundance for isotopes can be very different, the line intensities of absorption gas lines of different isotopologues can also be very different.

The current procedures of measuring the ratio of isotopologue concentrations in the gas phase by the optical spectroscopy method consist of measuring of optical spectra of a test sample, deriving the concentrations of different isotopogues in the tested gas based on the measured spectra, fitting them using spectral databases and line-shape models; measuring of optical spectra of one or more calibrated test samples, deriving the concentrations of different isotopogues in the calibrated samples based on the measured spectra, fitting them using spectral databases and line-shape models, and calculating the ratio of different isotopogues in the test sampe based on these measurements. A common procedure to measure the ratio of concentrations of different isotopologues in a gas mixture comprises periodical calibrations of an optical absorption based gas analyzers by using gas mixtures having known composition of the isotopologues. This procedure is rather expensive, time consuming, and it requires precisely calibrated gas mixtures.

Accordingly, it is desirable to provide improved spectroscopy methods for measuring concentrations of different isotopologues in their gas phase.

SUMMARY OF THE INVENTION

The present invention provides methods for measuring the ratio of concentrations of different gaseous isotopologues. Embodiments of the present invention provide methods for detecting the isotopic ratios of concentrations of different gaseous isotopologues in an analyzed gas mixture using optical absorption spectroscopy methods. If the methods are based on using an optical cavity, which contains a gas mixture to be analyzed, then one or more lasers coupled to the cavity, and one or more light sensitive detectors are used to measure absorption of laser light by gas mixture. The optical cavity can be a resonant optical cavity. A detection method can be based on a variety of cavity enhanced optical spectroscopy (CEOS) methods, for example, cavity ring-down spectroscopy (CRDS) methods, cavity phase shift spectroscopy methods, cavity enhanced absorption spectroscopy (CEAS) methods, integrated cavity output spectroscopy (ICOS), or cavity enhanced photo-acoustic spectroscopy (CE-PAS) methods. A detection method can also be based on tunable diode laser absorption spectroscopy (TD-LAS) methods with or without the use of a multipass cell. Photo-acoustic spectroscopy (PAS) can also be used as a detection method.

A method described in one embodiment is based on measuring spectral line intensities of two different rotational-vibrational lines of different rotational-vibrational bands of two isotopologues at some temperature using a first gas analyzer, finding the ratio of two line intensities, and comparing the ratio to another ratio determined from the same lines at the same temperature, but using a gas mixture with known isotopic composition and a different high performance gas analyzer. The method eliminates using calibrated gas mixtures for periodical calibration, but it is based on comparison of just one number to another number.

DETAILED DESCRIPTION OF THE INVENTION

Here and further we use the term "the spectral line intensity" in units of $[cm^{-1}/(molecule\ cm^{-2})]$ similar to what was given in FIG. 1 in the Appendix to the article on the 1996 Edition of HITRAN in the Journal of Quantitative Spectroscopy and Radiative Transfer vol. 60, pp. 665-710 (1998). However, in our case the spectral line intensities are specified per an isotopologue molecule, while the spectral line intensities that appear in HITRAN are weighted according to the natural terrestrial isotopic abundances.

Methods described herein may include or employ one or more spectrometers measuring rotational-vibrational spectra of different isotolologues in the gas phase. The rotational-vibrational spectra are often resolved into lines due to transitions from one rotational level in the ground vibrational state to one rotational level in the vibrationally excited state. The lines corresponding to a given vibrational transition form a band. According to a general convention rotational-vibrational bands can be divided into three branches: R-branch, P-branch, and Q-branch:

R branch: when $\Delta J=+1$, i.e. the rotational quantum number in the ground state is one more than the rotational quantum number in the excited state;

P branch: when $\Delta J=-1$, i.e. the rotational quantum number in the ground state is one less than the rotational quantum number in the excited state;

Q branch: when $\Delta J=0$, i.e. the rotational quantum number in the ground state is the same as the rotational quantum number in the excited state.

According to the methods a gas analyzer system measures rotational-vibrational spectra of isotopologues in the gas phase at least at two spectral regions: in a first spectral region the system measures a spectrum in vicinity of a first rotational-vibrational line of a first isotopologue, and in a second spectral region the system measures spectrum of a second rotational-vibrational line of a second isotopologue. Other lines of the same isotopologues or other isotopologues and other chemical species can also be located and measured in both spectral regions.

In general, to improve the system performance, these two lines belong to different vibrational modes chosen in such way that the spectral line intensities of a vibrational mode of a less abundant isotopologue are stronger than the spectral line intensities of another vibrational mode of a more abundant isotopologue. This approach permits to improve both the precision and the accuracy of the isotope ratio measurements because the line intensities of two measured lines might be closer to each other, in comparison with the case when two lines of the same vibrational modes of two isotopologues are measured. Notice, in general, for spectral analysis of gas mixtures containing different isotopologues one can choose rotational-vibrational lines with quite different spectral line intensities from the same vibrational modes of different isotopologues. However, in that case these lines usually have quite different pressure broadening and temperature dependences. So, the precise isotopic ratio analysis would require extremely accurate temperature and pressure stabilizations of the tested gas mixtures.

Figure 1:
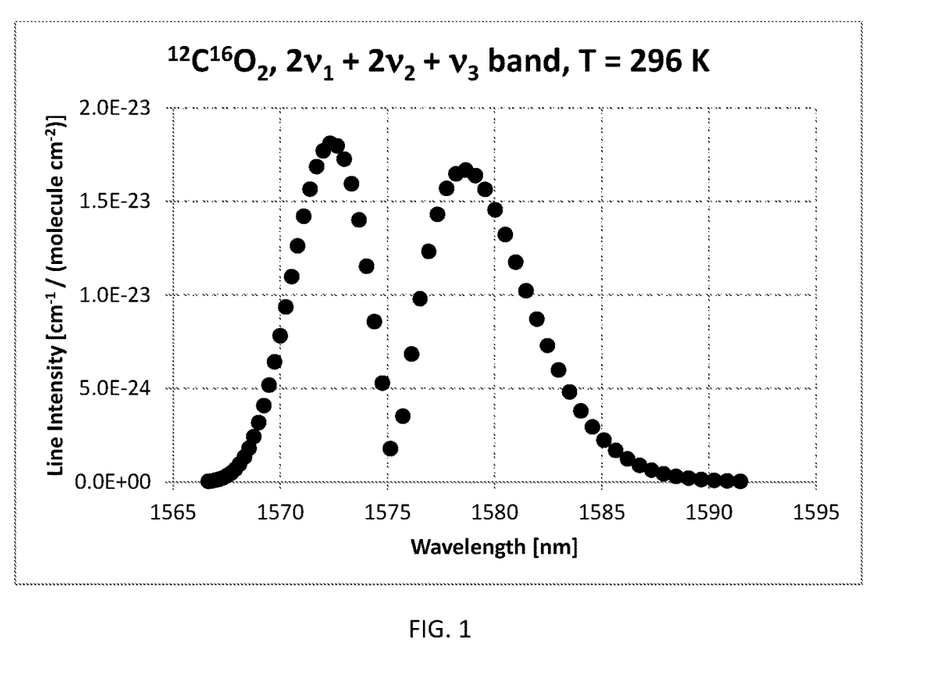
FIG. 1. Line intensities of different rotational-vibrational transitions from one rotational level in the ground vibrational state to one rotational level in the vibrationally excited state $2v_1+2v_2+v_3$ of $^{12}C^{16}O_2$ isotopologue at 296 K.
Figure 2:
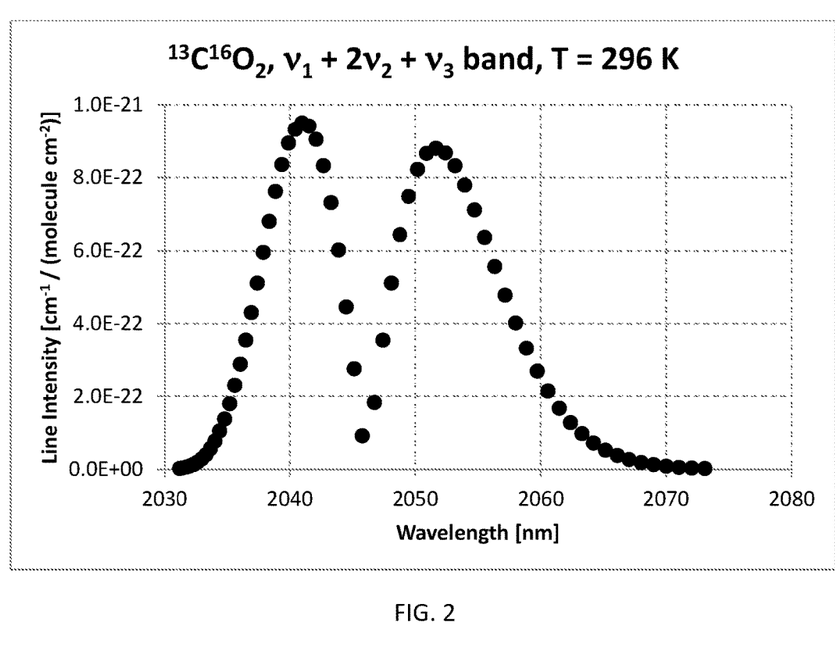
FIG. 2. Line intensities of different rotational-vibrational transitions from one rotational level in the ground vibrational state to one rotational level in the vibrationally excited state $v_1+2v_2+v_3$ of $^{13}C^{16}O_2$ isotopologue at 296 K.

FIG. 1 and FIG. 2 show examples of the line intensities of different vibrational modes of the two most abundant isotopologues of carbon dioxide in Mid-IR and NIR-IR spectral regions. Circles represent different rotational-vibrational transitions from one rotational level in the ground vibrational state to another rotational level in the vibrationally excited state. The line intensities were obtained from the HITRAN database. The energy change of rotation can be either subtracted from or added to the energy change of vibration, giving the P- and R- branches of the spectrum, respectively. Both P- and R branches are shown. Taking to account that abundance of carbon dioxide isotopologues, according to HITAN is 98.42% and 1.106% for $^{12}C^{16}O_2$ and $^{13}C^{16}O_2$, respectively, these pairs of rotational-vibrational bands can be considered for spectral analysis according to one of the embodiments. However, there are several combinations of rotational-vibrational bands which can be promising for high precision gas analysis of $^{12}C^{16}O_2$ and $^{13}C^{16}O_2$ isotopologues:

1) $v_1+v_3$ vibrational mode of $^{12}C^{16}O_2$ and $v_3$ vibrational mode of $^{13}C^{16}O_2$;
2) $v_1+2v_2+v_3$ vibrational mode of $^{12}C^{16}O_2$ and $v_3$ vibrational mode of $^{13}C^{16}O_2$;
3) $v_1+4v_2+v_3$ vibrational mode of $^{12}C^{16}O_2$ and $v_3$ vibrational mode of $^{13}C^{16}O_2$;
4) $2v_1+2v_2+v_3$ vibrational mode of $^{12}C^{16}O_2$ and $v_3$ vibrational mode of $^{13}C^{16}O_2$;
5) $v_1+2v_2+v_3$ vibrational mode of $^{12}C^{16}O_2$ and $v_1+v_3$ vibrational mode of $^{13}C^{16}O_2$;
6) $v_1+4v_2+v_3$ vibrational mode of $^{12}C^{16}O_2$ and $v_1+v_3$ vibrational mode of $^{13}C^{16}O_2$;
7) $2v_1+2v_2+v_3$ mode of for $^{12}C^{16}O_2$ and $v_1+v_3$ mode of $^{13}C^{16}O_2$;
8) $v_1+4v_2+v_3$ vibrational mode of $^{12}C^{16}O_2$ and $v_1+2v_2+v_3$ vibrational mode of $^{13}C^{16}O_2$;
9) $2v_1+2v_2+v_3$ vibrational mode of $^{12}C^{16}O_2$ and $v_1+2v_2+v_3$ vibrational mode of $^{13}C^{16}O_2$;

where $v_1$, $v_2$, and $v_3$ represent normal modes of the $CO_2$ molecule: symmetric stretch, bend, and asymmetric stretch, respectively.

By comparing FIGS. 1-2 one can easily see that the bands in these pairs are spectrally separated and the line intensity of the strongest line in the band of the less abundant isotopologue is about 50 times as strong as the line intensity of the strongest line in the band of the more abandon isotopologue.

Figure 3:
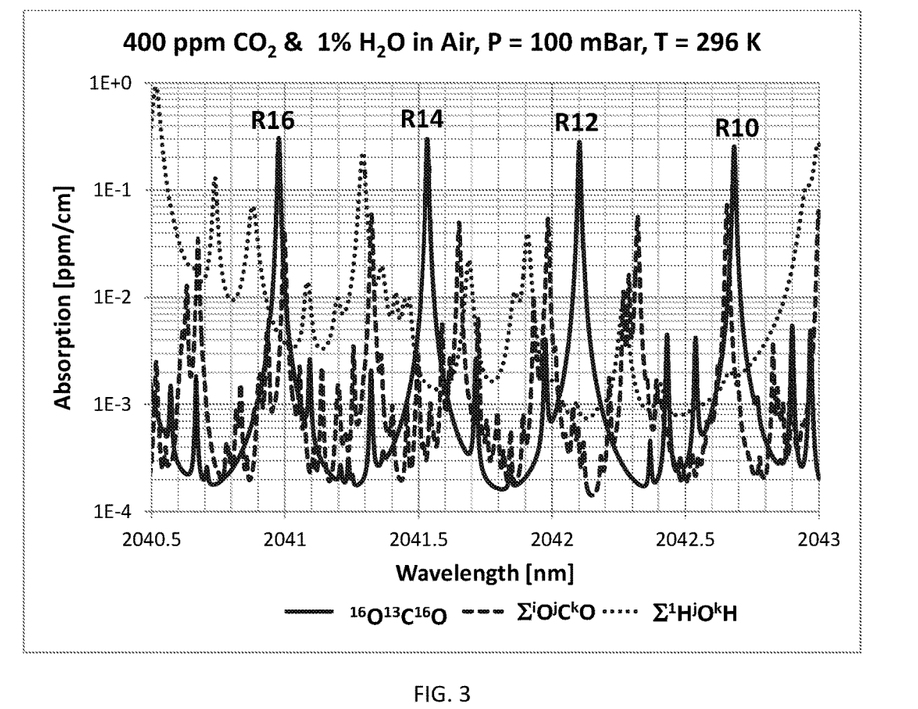
FIG. 3. Spectrum of the $^{13}C^{16}O_2$ isotopologue, the sum of spectra of all other isopologues of $CO_2$, and the sum of spectra of all isopologues of water from 2040.5 nm to 2043 nm at a pressure of 100 mBar and a temperature of 296 K. $R_x$ symbols show positions where the corresponding rotational-vibrational transitions, from one rotational level in the ground vibrational state to another rotational level in the vibrationally excited state $v_1+2v_2+v_3$ of $^{13}C^{16}O_2$ isotopologue, are located. The total concentration of carbon dioxide is 400 part per million. The total concentration of water is 1%.
Figure 4:
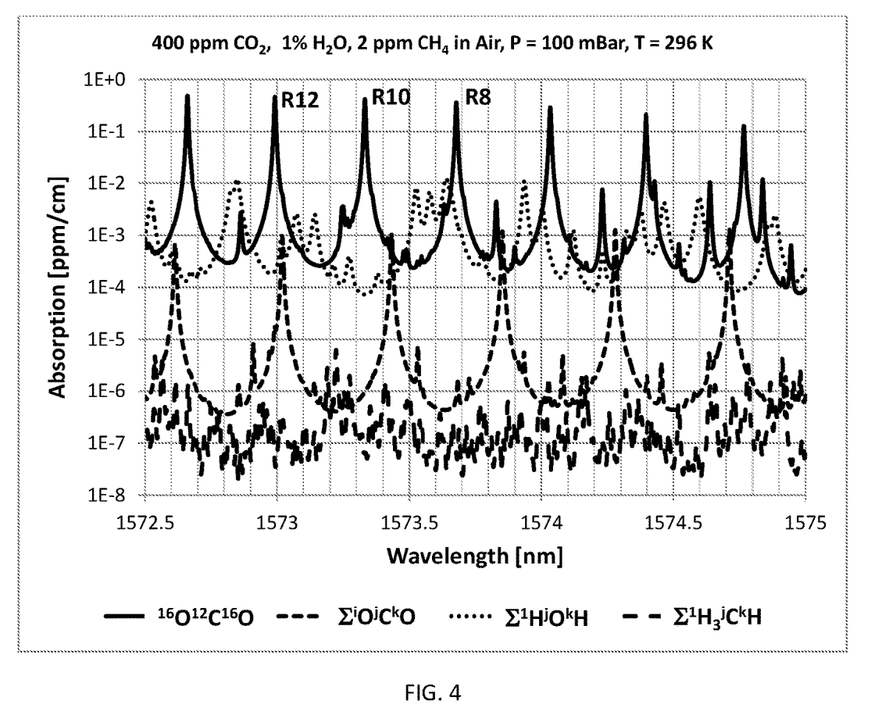
FIG. 4. Spectrum of the $^{12}C^{16}O_2$ isotopologue, the sum of spectra of all other isopologues of $CO_2$, the sum of spectra of all isopologues of water, and the sum of spectra of all isopologues of methane from 1572.5 nm to 1575 nm at a pressure of 100 mBar and a temperature of 296 K. $R_x$ symbols show positions where corresponding rotational-vibrational transitions from one rotational level in the ground vibrational state to another rotational level in the vibrationally excited state $2v_1+2v_2+v_3$ of $^{13}C^{16}O_2$ isotopologue are located. The total concentration of carbon dioxide is 400 part per million. The total concentration of water is 1%.

As an example, the R12 rotational-vibrational line of the $v_1+2v_2+v_3$ vibrational mode of $^{13}C^{16}O_2$ and the R10 rotational-vibrational line of the $2v_1+2v_2+v_3$ vibrational mode of $^{12}C^{16}O_2$ can be selected for isotopic ratio analysis. The first spectral range to measure lines of $^{13}C^{16}O_2$ is from 2040.5 nm to 2043 nm. The second spectral range to measure lines of $^{12}C^{16}O_2$ is from 1572.5 nm to 1575 nm. Notice, these rotational-vibrational lines correspond to quite different transitions from one rotational level in the ground vibrational state to one rotational level in the vibrationally excited state. For example, the R12 rotational-vibrational line of the $v_1+2v_2+v_3$ vibrational mode of $^{13}C^{16}O_2$ corresponds to the transition $(v_1=0, v_2=0, v_3=0, J=12) \rightarrow (v_1=1, v_2=2, v_3=1, J=13)$ from the rotation level $J=12$ of the ground state to the rotation level $J=13$ of the vibrationally excited $v_1+2v_2+v_3$ vibrational mode, or to $(\Delta v_1=+1, \Delta v_2=+2, \Delta v_1=+1, \Delta J=+1)$ transition, while the R10 rotational-vibrational line of $2v_1+2v_2+v_3$ vibrational mode of $^{12}C^{16}O_2$ corresponds to the transition $(v_1=0, v_2=0, v_3=0, J=10) \rightarrow (v_1=2, v_2=2, v_3=1, J=11)$ from the rotation level $J=10$ of the ground state to the rotation level $J=11$ of the vibrationally excited $2v_1+2v_2+v_3$ vibrational mode, or to $(\Delta v_1=+2, \Delta v_2=+2, \Delta v_1=1, \Delta J=+1)$ transition. FIGS. 3-4 were created for gas pressure $P=100$ mBar, and gas temperature $T=296K$. $\Sigma$ stands for sum, while indexes i, j, and k describe different isotopes of hydrogen, oxygen, or carbon atoms.

Described methods are based on a few assumptions: at a fixed temperature the ratio of the line intensities of different rotational-vibrational lines of an isotopologue is a constant; the ratio of two line intensities of different rotational-vibrational lines of an isotopologue is an injective (one-to-one) function of the gas temperature in some temperature range at least, and the line intensity is proportional to the isotopologue density in isotopologue molecules per volume units. In other words, if the ratio of two line intensities of different rotational-vibrational lines which belong to two different isotopologues is known, and the gas temperature is known, the ratio of concentrations of two isotopologues can be found.

According to an embodiment, a method is provided for performing an absorption measurement. The method typically includes selecting absorption lines of different isotopologues belonging to different rotational-vibrational bands, measuring absorption spectra vicinity these lines, and degerming the line intensities of these lines. The method also typically includes calculating the ratio of line intensities and comparing the said ratio to another ratio of two line intensities of different rotational-vibrational lines of the said isotopologues in a gas mixture having a known isotopic composition. The second ratio was measured using another, preferably very high accuracy, absorption spectroscopy based gas analyzer. The method also includes determining the ratio of concentrations of isotopologues based on values of two ratios and values of gas temperatures, when these ratios were measured.

According to another embodiment, a method is provided for performing an absorption measurement. The method typically includes selecting absorption lines of different isotopologues belonging to different rotational-vibrational bands, measuring absorption spectra vicinity these lines, and determining the line intensities of these lines. The method also typically includes calculating the ratio of line intensities and comparing the said ratio to another ratio of two line intensities of different rotational-vibrational lines of the said isotopologues in a gas mixture having a known isotopic composition. The second ratio was measured using another, preferably very high accuracy, absorption spectroscopy based gas analyzer. The method also includes determining the ratio of concentrations of isotopologues based on values of two ratios and values of gas temperatures, when these ratios were measured, wherein the ratio was measured at a standard temperature, such as 273.15 K, or the temperature of the triple point of water of 273.16 K, or at another temperature which can be easily reproduced and can serve as a standard temperature.

According to yet a further embodiment, a method is provided for performing an absorption measurement. The method typically includes selecting absorption lines of different isotopologues belonging to different rotational-vibrational bands, measuring absorption spectra vicinity these lines, and determining the line intensities of these lines. The method also typically includes calculating the ratio of line intensities and comparing the said ratio to another ratio of two line intensities of the same pair of rotational-vibrational lines of the said isotopologues in a gas mixture having a known isotopic composition. The second ratio was measured using another, preferably very high accuracy, absorption spectroscopy based gas analyzer. The method also includes determining the ratio of concentrations of isotopologues based on values of two ratios and values of gas temperatures, when these ratios were measured.

According to another embodiment, a method is provided for performing an absorption measurement. The method typically includes selecting absorption lines of different isotopologues belonging to different rotational-vibrational bands, measuring absorption spectra vicinity these lines, and determining the line intensities of these lines. The method also typically includes calculating the ratio of line intensities and comparing the said ratio to another ratio of two line intensities of different rotational-vibrational lines of the said isotopologues in a gas mixture having a known isotopic composition. The second ratio was measured using another, preferably very high accuracy, absorption spectroscopy based gas analyzer. The method also includes selecting another absorption line of the same rotational-vibrational bands used in the said measurements, determining the line intensity of this line and estimating the gas temperature based on the line intensities of two lines of the same rotational-vibrational band. The last procedure can be done for both analyzers. It permits to determine the ratio of concentrations of isotopologues based on values of four ratios wherein two ratios define the gas temperatures, when other two ratios defining isotopic compositions were measured.

The mentioned above methods rely on measuring the line intensities of different rotational-vibrational lines. However, if lines are not well separated it is hard to accurately measure their intensities. Moreover, if a laser cannot continuously be tuned over some spectral range, the line intensity determination includes using line shape models. However, if the laser frequency can be precisely measured or locked to specific wavelengths, one can measure gas absorbance at two wavelengths, preferably at one wavelength the light will be absorbed mostly by one isotopologue and at another wavelength the light will be absorbed mostly by another isotopologue.

According to another embodiment, a method is provided for performing an absorption measurement. The method typically includes selecting absorption lines of different isotopologues belonging to different rotational-vibrational bands, measuring the optical absorbances at two wavelengths at vicinity these lines. The method also typically includes calculating the ratio of these two absorbances and comparing the said ratio to another ratio of two absorbances at the same wavelengths of a gas mixture having a known isotopic composition. The second ratio was measured using another, preferably very high accuracy, absorption spectroscopy based gas analyzer. The method also includes determining the ratio of concentrations of isotopologues based on values of two ratios, values of gas temperatures, and values of gas pressures when these ratios were measured.

In certain aspects, the measurements of the absorbances can be done at maxima of rotational-vibrational lines. In certain aspects, the measurements of the absorbances can be done at local absorbance maxima adjusted to absorbance maxima of rotational-vibrational lines. The last method is using the gas spectroscopy as a precise wavemeter.

Recently, it was shown that a transmission line-shape of cesium (Cs) vapor can be used to define the Boltzmann's constant, the parameter that relates energy to temperature. A significant progress was made to define a new temperature standard based on the atomic spectroscopy method. A similar situation for the pressure standard which can be defined based on the laser interferometry and optical properties of gases. Moreover, the SI definition of second is "the duration of 9 192 631 770 periods of the radiation corresponding to the transition between the two hyperfine levels of the ground state of the cesium 133 atom", and the meter is defined as the length of the path travelled by light in a vacuum in 1/299,792,458 second.

However, the isotopic standard of $^{13}C/^{12}C$ is still defined by the ratio of $^{13}C/^{12}C$ in primary carbonate reference materials. Traditional stable isotope mass-spectrometry uses calibrations vs $CO_2$ evolved from the primary carbonate reference materials.

Embodiments of the present invention allow for the replacement of more complex procedure of preparation in reference gases for calibration of isotopic ratio gas analyzers with a simpler procedure of establishing of a primary optical transfer standard and secondary optical transfer standards based on the ratio of the line intensity of a rotational-vibrational line of a rotational-vibrational band of a first isotopologue and the line intensity of another second rotational-vibrational line of another second rotational-vibrational band of a second isotopologue at some specific gas temperature According to an embodiment, a method is provided for defining a primary optical transfer standard of the ratio of concentrations of two gaseous isotopologues of a chemical species. The method typically includes converting an isotopic standard medium into a gas phase medium by producing at least two gaseous isotopologues, and transferring gaseous isotopologues produced in the previous step into an optical absorption based gas analyzer. The method also typically includes stabilizing the gas temperature of the gas in the gas analyzer, measuring rotational-vibrational absorption spectra of the gas in two spectral regions. The method includes determining the line intensities of two rotational-vibrational lines of isotopologues and calculating the ratio of the line intensities. The method includes defining the primary optical transfer standard of the ratio of concentrations of two gaseous isotopologues as the ratio of the line intensities at temperature of the gas measured by optical absorption based gas analyzer.

According to another embodiment, a method is provided for defining a secondary optical transfer standard of the ratio of concentrations of two gaseous isotopologues of a chemical species by measuring rotational-vibrational absorption spectra of the gas at other spectral regions at the temperature of the primary standard, and defining the ratio of the line intensities of other two rotational-vibrational lines as the secondary optical transfer standard.

According to yet another embodiment, a method is provided for defining a secondary optical transfer standard of the ratio of concentrations of two gaseous isotopologues of a chemical species by measuring rotational-vibrational absorption spectra of the gas at other spectral regions at a temperature different from the temperature of the primary standard, and defining the ratio of the line intensities of other two rotational-vibrational lines as the secondary optical transfer standard.

The invention claimed is:

1. A method of measuring a ratio of concentrations of two isotopologues of a chemical species in a first gas mixture using a first optical absorption spectroscopy based gas analyzer, the method comprising the steps of: i) measuring optical absorption spectra of the first gas mixture in a first spectral range containing a first rotational-vibrational line of a first rotational-vibrational band of a first isotopologue and in a second spectral range containing a second rotational-vibrational line of a second rotational-vibrational band of a second isotopologue at a first gas temperature; ii) based on the measured spectra determining the line intensity of the first rotational-vibrational line of the first rotational-vibrational band of the first isotopologue and the line intensity of the second rotational-vibrational line of the second rotational-vibrational band of the second isotopologue at the first gas temperature; iii) determining a first ratio of the line intensity of the first rotational-vibrational line and the line intensity of the second rotational-vibrational line at the first gas temperature; iv) comparing the first ratio to a second ratio of the line intensity of a third rotational-vibrational line of a third rotational-vibrational band of the first isotopologue and the line intensity of a fourth rotational-vibrational line of a fourth rotational-vibrational band of the second isotopologue in a second gas mixture at a second gas temperature, the second gas mixture having a known ratio of concentrations of two said isotopologues, wherein the second ratio was determined using a second optical absorption spectroscopy based gas analyzer; v) calculating the ratio of concentrations of the said isotopologues in the first gas mixture.

2. The method of claim 1, wherein the second ratio of the line intensity of the third rotational-vibrational line of the third rotational-vibrational band of the first isotopologue and the line intensity of the fourth rotational-vibrational line of the fourth rotational-vibrational band of the second isotopologue in the second gas mixture at a second gas temperature is calculated based on the ratio of the line intensity of the third rotational-vibrational line of the third rotational-vibrational band of the first isotopologue and the line intensity of the fourth rotational-vibrational line of the fourth rotational-vibrational band of the second isotopologue of the second gas mixture having the known ratio of concentrations of two said isotopologues at the standard temperature.

3. The method of claim 1, wherein the first rotational-vibrational line of the first rotational-vibrational band of the first isotopologue is the same as the third rotational-vibrational line of the third rotational-vibrational band of the first isotopologue and the second rotational-vibrational line of the second rotational-vibrational band of the second isotopologue is the same as the fourth rotational-vibrational line of the fourth rotational-vibrational band of the second isotopologue.

4. The method of claim 1, further comprising the steps of: i) measuring an optical absorption spectrum in a fifth spectral range containing a fifth rotational-vibrational line of the first rotational-vibrational band of the first isotopologue; ii) based on the measured spectrum determining the line intensity of the fifth rotational-vibrational line of the first rotational-vibrational band of the first isotopologue; iii) determining the first gas temperature of the first gas mixture from the ratio of the line intensity of the first rotational-vibrational line and the line intensity of the fifth rotational-vibrational line.

5. A method of measuring a ratio of concentrations of two isotopologues of a chemical species in a first gas mixture using a first optical absorption spectroscopy based gas analyzer, the method comprising the steps of: i) measuring an optical absorbance of the first gas mixture at a first wavelength in a first spectral range containing a first rotational-vibrational line of a first rotational-vibrational band of a first isotopologue and an optical absorbance of the first gas mixture at a second wavelength in a second spectral range containing a second rotational-vibrational line of a second rotational-vibrational band of a second isotopologue at a first gas temperature and at a first gas pressure; ii) determining a first ratio of two said optical absorbances at the first gas temperature; iii) comparing the first ratio to a second ratio of the optical absorbance at the first wavelength and the optical absorbance at the second wavelength of a second gas mixture at a second gas temperature and a second gas pressure, where the second gas mixture having a known ratio of concentrations of two said isotopologues, wherein the second ratio was determined using a second optical absorption spectroscopy based gas analyzer; iv) calculating the ratio of concentrations of the said isotopologues in the first gas mixture.

6. The method of claim 5, wherein the first gas temperature and the second gas temperature are different by no more than 1 K and the first gas pressure and the second gas pressure are different by no more than 10 mBar.

7. The method of claim 5, wherein the first wavelength is at the maximum of the first rotational-vibrational line of the first rotational-vibrational band of the first isotopologue and the second wavelength is at the maximum of the second rotational-vibrational line of the second rotational-vibrational band of the second isotopologue at the second gas temperature and at the second gas pressure of the first gas mixture.

8. The method of claim 5, wherein the first wavelength is at a first local absorbance maximum closest to the maximum of the first rotational-vibrational line of the first rotational-vibrational band of the first isotopologue and the second wavelength is at a second local absorbance maximum closest to the maximum of the second rotational-vibrational line from the second rotational-vibrational band of the second isotopologue at the second gas temperature and at the second gas pressure of the first gas mixture.

9. A method for defining a primary optical transfer standard of the ratio of concentrations of two gaseous isotopologues of a chemical species, the method comprising the steps of: i) converting a first isotopic standard medium into a gas phase medium by producing a first gaseous isotopologue and a second gaseous isotopologue containing the type of atoms defined for the isotopic standard by first medium, unless the first medium is already in the gas phase; ii) transferring gaseous isotopologues produced in the previous step into an optical absorption based gas analyzer, iii) stabilizing the gas temperature of the gas transferred into the said gas analyzer at a first temperature, iv) measuring rotational-vibrational absorption spectra of the said gas in a first spectral range containing a first rotational-vibrational line of a first rotational-vibrational band of the first isotopologue and in a second spectral range containing of a second rotational-vibrational line of a second rotational-vibrational band of the second isotopologue at the first gas temperature; v) based on the said spectra determining the line intensity of the first rotational-vibrational line of the first rotational-vibrational band of the first isotopologue and the line intensity of the second rotational-vibrational line of the second rotational-vibrational band of the second isotopologue at the first gas temperature; vi) defining a first ratio of the line intensity of the first rotational-vibrational line and the line intensity of the second rotational-vibrational line at the first gas temperature; vii) defining the primary optical transfer standard of the ratio of concentrations of two gaseous isotopologues as the first ratio of the line intensity of the first rotational-vibrational line of the first rotational-vibrational band of the first isotopologue and the line intensity of the second rotational-vibrational line of the second rotational-vibrational band of the second isotopologue at the first gas temperature.

10. The method of claim 9, wherein the first temperature is the standard temperature of 273.15 K or the temperature of the triple point of water of 273.16 K.

11. The method of claim 9, further comprising the steps of: i) measuring rotational-vibrational absorption spectra of the said gas in a third spectral range containing a third rotational-vibrational line of a third rotational-vibrational band of the first isotopologue and in a fourth spectral range containing a fourth rotational-vibrational line of a fourth rotational-vibrational band of the second isotopologue at the first gas temperature; ii) based on the said spectra determining the line intensity of the third rotational-vibrational line of the third rotational-vibrational band of the first isotopologue and the line intensity of the fourth rotational-vibrational line of the fourth rotational-vibrational band of the second isotopologue at the first gas temperature; iii) determining a second ratio of the line intensity of the third rotational-vibrational line and the line intensity of the fourth rotational-vibrational line at the first gas temperature; iv) defining a secondary optical transfer standard of the ratio of concentrations of two gaseous isotopologues as the second ratio of the line intensity of the third rotational-vibrational line of the third rotational-vibrational band of the first isotopologue and the line intensity of the fourth rotational-vibrational line of the fourth rotational-vibrational band of the second isotopologue at the first gas temperature.

12. The method of claim 9, further comprising the steps of: i) measuring rotational-vibrational absorption spectra of the said gas in a first spectral range containing the first rotational-vibrational line of the first rotational-vibrational band of the first isotopologue and in a second spectral range containing the second rotational-vibrational line of the second rotational-vibrational band of the second isotopologue at a second gas temperature; ii) based on the said spectra determining the line intensity of the first rotational-vibrational line of the first rotational-vibrational band of the first isotopologue and the line intensity of the second rotational-vibrational line of the second rotational-vibrational band of the second isotopologue at the second gas temperature; iii) determining a second ratio of the line intensity of the first rotational-vibrational line and the line intensity of the second rotational-vibrational line at the second gas temperature; iv) defining a secondary optical transfer standard for the ratio of concentrations of two gaseous isotopologues as the second ratio of the line intensity of the first rotational-vibrational line of the first rotational-vibrational band of the first isotopologue and the line intensity of the second rotational-vibrational line of the second rotational-vibrational band of the second isotopologue at the second gas temperature.

13. The method of claim 9, further comprising the steps of: i) measuring rotational-vibrational absorption spectra of the said gas in a third spectral range containing a third rotational-vibrational line of a third rotational-vibrational band of the first isotopologue and in a fourth spectral range containing a fourth rotational-vibrational line of a fourth rotational-vibrational band of the second isotopologue at a second gas temperature; ii) based on the said spectra determining the line intensity of the third rotational-vibrational line of the third rotational-vibrational band of the first isotopologue and the line intensity of the fourth rotational-vibrational line of the fourth rotational-vibrational band of the second isotopologue at the second gas temperature; iii) determining a second ratio of the line intensity of the third rotational-vibrational line and the line intensity of the fourth rotational-vibrational line at the second gas temperature; iv) defining a secondary optical transfer standard for the ratio of concentrations of two gaseous isotopologues as the second ratio of the line intensity of the third rotational-vibrational line of the third rotational-vibrational band of the first isotopologue and the line intensity of the fourth rotational-vibrational line of the fourth rotational-vibrational band of the fourth isotopologue at the second gas temperature.

14. The method of claim 9, further comprising the steps of: i) measuring rotational-vibrational absorption spectrum of the said gas in a third spectral range containing a third rotational-vibrational line of first rotational-vibrational band of the first isotopologue; ii) based on the said spectrum determining the line intensity of the third rotational-vibrational line of the first rotational-vibrational band of the first; iii) determining a second ratio of the line intensity of the first rotational-vibrational line of first rotational-vibrational band of the first isotopologue and the line intensity of the third rotational-vibrational line of first rotational-vibrational band of the first isotopologue; iv) defining a secondary optical transfer standard of the ratio of concentrations of two gaseous isotopologues as the first ratio of the line intensity of the first rotational-vibrational line of the first rotational-vibrational band of the first isotopologue and the line intensity of the second rotational-vibrational line of the second rotational-vibrational band of the second isotopologue at the second ratio of the line intensity of the first rotational-vibrational line of first rotational-vibrational band of the first isotopologue and the line intensity of the third rotational-vibrational line of first rotational-vibrational band of the first isotopologue.

* * * * *